United States Patent [19]

Favre-Bulle et al.

[11] Patent Number: 5,616,498
[45] Date of Patent: Apr. 1, 1997

[54] BIOLOGICAL REMOVAL OF DIHALOCARBOXYLIC ACID IRRITANTS

[75] Inventors: Olivier Favre-Bulle; Jean-Marc Ricca, both of Lyons, France

[73] Assignee: Rhone-Poulenc Chimie, Courbevoie Cedex, France

[21] Appl. No.: 508,171

[22] Filed: Jul. 27, 1995

[30] Foreign Application Priority Data

Jul. 27, 1994 [FR] France ................................. 94 09287

[51] Int. Cl.$^6$ ................................................. D06M 16/00
[52] U.S. Cl. .......................................... 435/264; 435/262.5
[58] Field of Search ................................. 435/264, 262.5

[56] References Cited

FOREIGN PATENT DOCUMENTS 0510987  10/1992  European Pat. Off. .
9320223  10/1993  WIPO .

OTHER PUBLICATIONS

Journal of Bacteriology, vol. 163, No. 2, Aug. 1985, pp. 635–639, Keuning et al.

Primary Examiner—Carolyn Paden
Attorney, Agent, or Firm—Burns, Doane, Swecker & Mathis, L.L.P.

[57] ABSTRACT

Contaminating trace amounts of byproduct dihalocarboxylic acids or salts thereof are removed from aqueous solutions which comprise less than 1,000 ppm of same and at least 20% by weight of amino acids or amino acid derivatives, to render such aqueous solutions nonirritating to biological membranes and suitable for cosmeticology applications, by directly contacting the original aqueous solutions with either (a) about 1 to 100 ppm of a microorganism producing an enzyme specific for the decomposition of said dihalocarboxylic acids or salts thereof, or (b) about 0.1 to 10 ppm of such enzyme, per se.

14 Claims, No Drawings

BIOLOGICAL REMOVAL OF DIHALOCARBOXYLIC ACID IRRITANTS

BACKGROUND OF THE INVENTION

1. Technical Field of the Invention

The present invention relates to a biological technique for removing contaminating trace amounts of dihalocarboxylic acids or salts thereof from aqueous solutions of amino acids or amino acid derivatives by treating such solutions with a minor amount of either a microorganism producing an enzyme specific for the decomposition of dihalocarboxylic acids or salts thereof, or with such enzyme, per se.

2. Description of the Prior Art

Aqueous solutions of amino acids or derivatives thereof are especially useful in the field of cosmeticology as surfactants or sequestering agents; since these solutions are contacted with biological entities or membranes, the presence of any impurity likely to contribute to irritation should be avoided.

Among the products and compounds that contribute to irritation, e.g., skin irritation, the dihalocarboxylic acids and salts thereof are especially representative.

Amino acids are typically prepared by condensing an aqueous solution of an amino compound with a halocarboxylic acid or derivative thereof. As a result of their own preparative technique, halocarboxylic acids or derivatives thereof may contain up to 5% by weight of byproduct dihalocarboxylic (in particular dichloro- or dibromocarboxylic) acid.

For example, α-amino-substituted acetic acids of the formula:

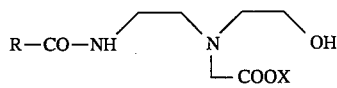

in which R is H, an alkyl or alkoxy radical and X is H, an alkali metal or alkaline earth metal or an ammonium residue, are traditionally prepared by condensing a secondary amine of the formula:

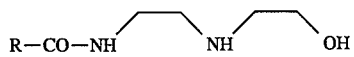

with chloroacetic acid or salt thereof, in particular sodium chloroacetate.

It has been determined that the final product aqueous solutions may contain up to 500 ppm of dichloroacetic acid or salt thereof. Such amounts can be decreased to 50 ppm by employing a purified chloroacetic acid, but the added cost militates against the economic viability of the final products for their intended applications.

WO-93/20,223 describes decomposing the haloalkanoic acids present as impurities in surfactants by contacting same with a dehalogenase enzyme.

Thus, the monochloropropionic or monochloroacetic acids or sodium salts thereof, present in a proportion of several g/l in aqueous solutions containing 12% by weight of surfactants (ether carboxylates in particular) buffered to pH 7.2 are hydrolyzed by means of *Pseudomonas putida* NCIB 12018; the organism is employed in the proportion of 2 g/l, namely, 2,000 ppm relative to the medium.

Nonetheless, the aqueous solutions obtained contain an amount of residual cells which are incompatible, from a standpoint both of performance and of biological tolerance, with applications in cosmeticology.

SUMMARY OF THE INVENTION

It has now unexpectedly been found that trace amounts of dihalocarboxylic acids or salts thereof can be removed from aqueous solutions containing at least 20% by weight of amino acids or amino acid derivatives and less than 1,000 ppm (parts by weight per million), and preferably less than 200 ppm, of dihalocarboxylic acids or salts thereof, by directly treating same with on the order of 1 to 100 ppm (parts by weight per million), and preferably on the order of 10 to 50 ppm, of a microorganism producing or expressing an enzyme specific for the decomposition of dihalocarboxylic acids or salts thereof, or with on the order of 0.1 to 10 ppm, and preferably on the order of 1 to 5 ppm, of such an enzyme, per se.

DETAILED DESCRIPTION OF BEST MODE AND PREFERRED EMBODIMENTS OF THE INVENTION

More particularly according to the present invention, especially representative enzymes specific for the decomposition of dihalocarboxylic acids or salts thereof are those capable of hydrolyzing dichloroacetic acid or dichloroacetic acid salts (alkali metal and ammonium salts).

These enzymes emanate from microorganisms determined by directly contacting same with dichloroacetic acid or salts thereof, under conditions well known to this art (*Manual of Methods for General Bacteriology*, American Society for Microbiology (1981)).

Microorganisms which hydrolyze at least 10% by weight of dichloroacetic acid or salts thereof, such as microorganisms of the genus Xanthobacter in particular, and more especially *Xanthobacter autotrophicus* ATCC 43050, are particularly suitable.

According to the present invention, the microorganism may be used as is or immobilized on supports well known to this art, such as polyacrylamide gels, carrageenan, alginates, and the like, or resins such as those of the Amberlite® type in the presence of a crosslinking agent of the polyethyleneimide type.

The microorganism may also be mutated via mutagenic agents or by genetic engineering according to techniques well known to this art (Ornston et al, *Journal of Biological Chemistry*, Vol. 241, p. 3800–3810).

Moreover, the genetic code for the enzyme may be transferred from the parent microorganism (such as *Xanthobacter autotrophicus*) to a nonpathogenic adapted microorganism not naturally containing this genetic information (such as *Escherichia coli*, *Bacillus subtilis*).

In another embodiment of the invention, in place of the microorganism, a corresponding amount of its enzyme, per se, free or immobilized, is employed, the enzyme either being completely or partially purified, and being employed in amounts ranging from about 0.1 to 10 ppm, preferably from 1 to 5 ppm.

The treatment according to this invention is advantageously carried out at a temperature on the order of 5° to 50° C., and preferably on the order of 10° to 40° C., depending on the thermal stability of the enzyme, at a pH on the order of 8 to 12, and preferably on the order of 8.5 to 10.

This treatment can be carried out for about 1 to 24 hours, and preferably 1 to 4 hours.

Particularly exemplary amino acids or derivatives thereof which can be treated according to the technique of the present invention include the following:

(1) surfactants of the amphoteric type, including alkylbetaines, alkylamidopropylbetaines, imidazoline compounds such as alkylamphoacetates and -diacetates, alkylhydroxyethyl- and alkyldihydroxyethylglycinates, and the like;

(2) sequestering agents such as ethylenediaminetetraacetic acid (EDTA), N-(hydroxyethyl)ethylenediaminetriacetic acid (HEEDTA), nitrilotriacetic acid (NTA), diethylenetriaminepentaacetic acid (DTPA), and the like, which agents may be obtained by condensing an aqueous solution of an amino compound with a halocarboxylic acid or derivative thereof.

The treatment according to this invention can be carried out either directly, at the end of the condensation reaction, or during storage of the final product.

It has been determined that the contents of dihalocarboxylic acid are less than 50 ppm, or even below the detection limits of the analytical techniques conventionally employed in this art, such as, for example, ion-exchange chromatography.

The method of the invention presents many advantages, namely:

(a) as a result of the small amounts of microorganisms employed, the integrity of the product treated (aqueous solutions of amino acids or derivatives thereof) is preserved both from the standpoint of its performance in use and from the standpoint of biological tolerance;

(b) the use, for the preparation of said product to be treated, of any commercial halocarboxylic acid, irrespective of its content of dihalocarboxylic impurity;

(c) the option of treating the product as is, without prior processing thereof.

In order to further illustrate the present invention and the advantages thereof, the following specific examples are given, it being understood that same are intended only as illustrative and in nowise limitative.

EXAMPLE 1

Culture of the microorganism:

*Xanthobacter autotrophicus* strain ATCC 43050 was cultured in a stirred flask at 30° C. for 48 hours, either in NB ("nutrient broth") medium or in medium A, the compositions of which were as follows:

NB medium:

| | |
|---|---|
| Beef extract | 3 g/l |
| Peptone | 5 g/l |
| NaCl | 8 g/l |
| pH 7.3 | |

Medium A:

| | |
|---|---|
| Succinate | 5 g/l |
| Dichloroacetate | 10 mM |
| $Na_2HPO_4$ | 5.7 g/l |
| $KH_2PO_4$ | 1.4 g/l |
| $(NH_4)_2SO_4$ | 0.5 g/l |
| $MgSO_4.7H_2O$ | 0.2 g/l |
| Yeast extract | 0.1 g/l |
| $FeSO_4.7H_2O$ | 20 mg/l |
| $MnSO_4.H_2O$ | 10 mg/l |
| pH 7.2 | |

The biomass obtained was separated by centrifugation and was then resuspended in NaCl solution, concentration 9 g/l.

Treatment:

A commercial aqueous solution of cocoylamphodicarboxylate containing 30% by weight of active agents, 11% by weight of NaCl, 7% by weight of sodium glycolate and 270 ppm of sodium dichloroacetate and having a pH of 8.5 was treated for 24 hours at 25° C. with 50 ppm of cells emanating from the above media.

The residual sodium dichloroacetate was measured by ion-exchange chromatography. The results obtained were as follows:

| Culture | Residual sodium dichloroacetate (ppm) |
|---|---|
| Control (without cells) | 270 |
| NB | 223 |
| A | 33 |

EXAMPLE 2

Culture of the microorganism:

*Xanthobacter autotrophicus* strain ATCC 43050 was cultured in a stirred flask at 30° C. for 48 hours in medium B, the composition of which was as follows:

Medium B:

| | |
|---|---|
| Dichloroacetate | 25 mM |
| $Na_2HPO_4$ | 5.7 g/l |
| $KH_2PO_4$ | 1.4 g/l |
| $(NH_4)_2SO_4$ | 0.5 g/l |
| $MgSO_4.7H_2O$ | 0.2 g/l |
| Yeast extract | 0.1 g/l |
| $FeSO_4.7H_2O$ | 20 mg/l |
| $MnSO_4.H_2O$ | 10 mg/l |
| pH 7.2 | |

The biomass obtained was separated by centrifugation and was then resuspended in NaCl solution, concentration 9 g/l.

Treatment:

A commercial aqueous solution of cocoylamphodicarboxylate containing 30% by weight of active agents, 11% by weight of NaCl, 7% by weight of sodium glycolate and 270 ppm of sodium dichloroacetate and having a pH of 8.5 was treated for 24 hours at 25° C. with 10 ppm of cells emanating from the above medium.

The level of residual sodium dichloroacetate, measured by ion-exchange chromatography, was less than 25 ppm, the detection limit of the apparatus.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for removing trace amounts of dihalocarboxylic acids or salts thereof from aqueous solutions which comprise less than 1,000 ppm thereof and at least 20% by weight of amino acids or amino acid derivatives, comprising directly contacting such aqueous solution with either (a) about 1 to 100 ppm of a microorganism producing an enzyme specific for the decomposition of said dihalocarboxylic acids or salts thereof, or (b) about 0.1 to 10 ppm of such enzyme, per se.

2. The method as defined by claim 1, comprising directly contacting said aqueous solution with said microorganism.

3. The method as defined by claim 2, said microorganism being of the genus Xanthobacter.

4. The method as defined by claim 3, said microorganism being of the species *Xanthobacter autotrophicus* ATCC 43050.

5. The method as defined by claim 2 comprising directly contacting said aqueous solution with about 10 to 50 ppm of said microorganism.

6. The method as defined by claim 1, comprising directly contacting said aqueous solution with said enzyme, per se.

7. The method as defined by claim 6, comprising directly contacting said aqueous solution with about 1 to 5 ppm of such enzyme, per se.

8. The method as defined by claim 1, said enzyme being specific for the decomposition of dichloroacetic acid or salt thereof.

9. The method as defined by claim 1, carried out at a temperature ranging from about 5° to 50° C., at a pH of about 8 to 12.

10. The method as defined by claim 9, carried out at a temperature ranging from about 10° to 40° C., at a pH of about 8.5 to 10.

11. The method as defined by claim 1, said amino acids or amino acid derivatives comprising an alkylbetaine, an alkylamidopropylbetaine, an alkylamphoacetate or -diacetate, an alkylhydroxyethyl- or alkyldihydroxyethylglycinate, ethylenediaminetetraacetic acid (EDTA), N-(hydroxyethyl)ethylenediaminetriacetic acid (HEEDTA), nitrilotriacetic acid (NTA), or diethylenetriaminepentaacetic acid (DTPA).

12. The method as defined by claim 1, said aqueous solution comprising less than 200 ppm of said dihalocarboxylic acids or salts thereof.

13. The nonirritating aqueous solution product of the method as defined by claim 1.

14. An aqueous solution comprising at least 20% by weight of amino acids or amino acid derivatives and some, but less than a biologically irritating amount of a dihalocarboxylic acid or salt thereof.

* * * * *